Figure 1:
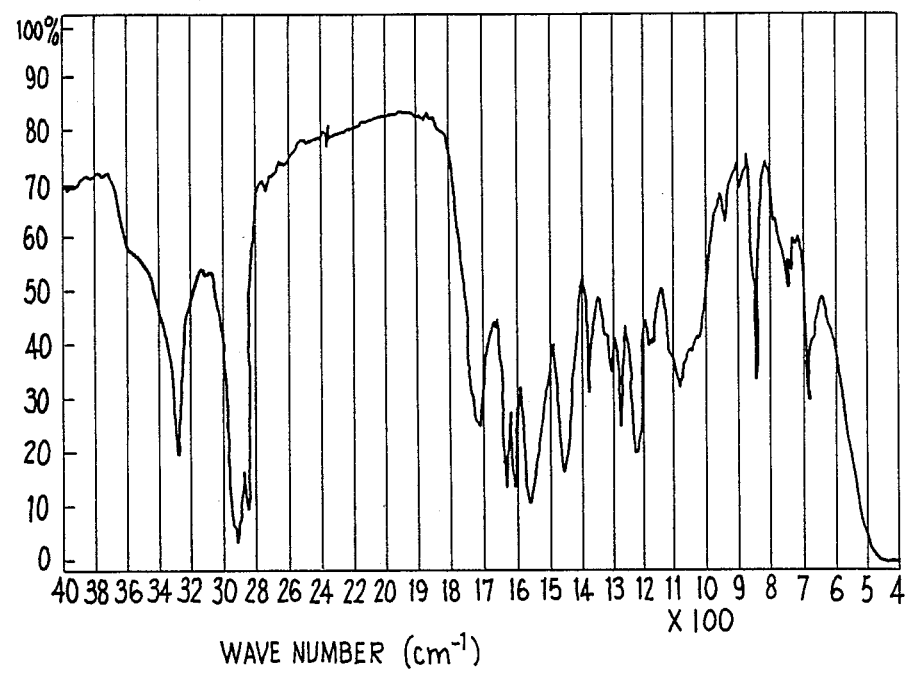

United States Patent [19]

Okamoto et al.

[11] Patent Number: 4,912,205

[45] Date of Patent: Mar. 27, 1990

[54] ALKYL-SUBSTITUTED PHENYLCARBAMATE DERIVATIVE OF POLYSACCHARIDE

[75] Inventors: Yoshio Okamoto, Amagasaki; Koichi Hatada, Ikeda, both of Japan

[73] Assignee: Daicel Chemical Industries, Ltd., Osaka, Japan

[21] Appl. No.: 24,741

[22] Filed: Mar. 11, 1987

[30] Foreign Application Priority Data

Mar. 20, 1986 [JP] Japan ................... 61-62828

[51] Int. Cl.$^4$ ............... C07B 57/00; C08B 31/00; C08B 37/00
[52] U.S. Cl. ..................... 536/20; 536/18.7; 210/656
[58] Field of Search ............ 536/20, 18.7; 210/656

[56] References Cited

FOREIGN PATENT DOCUMENTS 0157365 10/1985 European Pat. Off. .
2101630 3/1972 France .

OTHER PUBLICATIONS

C. E. Carraer et al.: "Modifications of Polymers", 1980, pp. 371–380, Chapter 24, American Chemical Society, Washington, U.S.

C. L. McCormick et al.: "Homogeneous Solution Reactions of Cellulose, Chitin, and other Polysaccharides", pp. 372–375.

*Primary Examiner*—Ronald W. Griffin
*Attorney, Agent, or Firm*—Flynn, Thiel, Boutell & Tanis

[57] ABSTRACT

A new alkyl-substituted phenylcarbamate derivative of a polysaccharide, exclusive of cellulose, has an alkyl-substituted phenylcarbamoyl group for 80 to 100 percent of the hydroxyl groups attached to the polysaccharide and is useful to the optical resolution of racemic compounds.

9 Claims, 1 Drawing Sheet

ALKYL-SUBSTITUTED PHENYLCARBAMATE DERIVATIVE OF POLYSACCHARIDE

CROSS REFERENCE TO RELATED APPLICATION

This application is related to Ser. No. 07/160 539, filed Feb. 26, 1988.

The present invention relates to an alkyl-substituted phenylcarbamate derivative of a polysaccharide, which is a novel polymer very valuable as a functional material.

It is known that a packing for a liquid chromatographic column comprising cellulose trisphenylcarbamate as the stationary phase has an excellent optical resolving capacity. See Journal of the American Chemical Society, 106, 5357 (1984) by Okamoto, Hatada et al.

We have made research on carbamate derivatives of polysaccharides other than cellulose and, as a result, have found that an alkyl-substituted phenylcarbamate derivative of a polysaccharide, exclusive of cellulose, can be easily prepared and has an excellent asymmetry-discriminating capacity. We have now completed the present invention based on this finding.

The invention provides a new alkyl-substituted phenylcarbamate derivative of a polysaccharide, exclusive of cellulose, in which 80 to 100 percent of the hydroxyl groups attached to the polysaccharide have been substituted by an alkyl-substituted phenylcarbamoyl group having the formula (I):

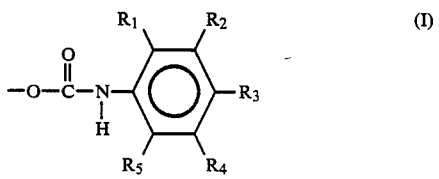

in which R1 to R5 each are hydrogen or an alkyl having 1 to 8 carbon atoms, provided that at least one of R1 to R5 is the alkyl.

It is preferable that the polysaccharide is optically active and has a polymerization degree of 5 to 500.

The invention further provides a separating agent comprising the alkyl-substituted phenylcarbamate derivative as defined above and a method for separating racemic compounds into isomers thereof by bringing them in contact with the derivative as defined above.

Any synthetic polysaccharides, natural polysaccharides and modified natural polysaccharides which are optically active can be used as the polysaccharide in the present invention, but a polysaccharide having a high regularity in the bonding manner is preferred. For example, there can be mentioned α-1,4-glucan (amylose and amylopectin), α-1,6-glucan (dextran), β-1,6-glucan (pustulan), β-1,3-glucan (such as curdlan or shizophyllan), α-1,3-glucan, β-1,2-glucan (crown gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, β-1,4-N-acetylchitosan (chitin), pullulan, agarose and alginic acid. Moreover, starch containing amylose is included. Amylose, β-1,4-chitosan, chitin, β-1,4-mannan, β-1,4-xylan, inulin and curdlan are especially preferred, because polysaccharides having a high purity can be easily obtained therefrom.

The number-average degree of polymerization (the average number of pyranose or furanose rings obtained in one molecule) is at least 5, preferably at least 10. The upper limit of the number-average degree of polymerization is not particularly critical. However, in view of the easiness of handling, it is preferred that the number-average degree of polymerization be lower than 500.

The carbamoyl group of the polysaccharide carbamate derivative of the present invention is represented by the following general formula (II), and 80 to 100% of hydroxyl groups of the corresponding polysaccharide form urethane linkages with the carbamoyl group, while remaining 20 to 0% of the hydroxyl groups may be substituted otherwise, though generally hydrogen atoms:

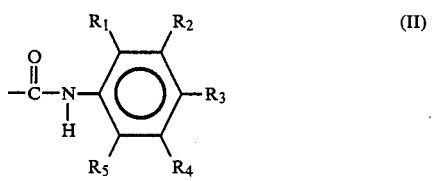

In the general formula (II), $R_1$ through $R_5$ stand for each a hydrogen atom or an alkyl group having 1 to 8 carbon atoms, preferably a hydrogen atom or a methyl group, with the proviso that at least one of $R_1$ through $R_5$ stands for an alkyl group having 1 to 8 carbon atoms, preferably a methyl group.

The reaction ordinarily adopted for forming a urethane from an alcohol and an isocyanate can be directly applied to the synthesis of the carbamate derivative of the present invention. For example, the carbamate derivative of the present invention can be synthesized by reacting a corresponding polysaccharide with a corresponding isocyanate in an appropriate solvent in the presence of a Lewis base such as a tertiary amine or a Lewis acid such as a tin compound as the catalyst. Furthermore, the isocyanate can be easily synthesized by reacting an amino group of a corresponding aniline derivative with phosgene.

When the polysaccharide carbamate derivative of the present invention is used as the separating agent for separating a compound or its optical isomer, there may be used generally adopted chromatographical methods such as gas chromatography, liquid chromatography and thin-layer chromatography. Furthermore, the polysaccharide carbamate derivative of the present invention can be applied to the separation method using a membrane.

When the polysaccharide carbamate derivative of the present invention is used for liquid chromatography, the derivative is generally packed in the powdery form into a column, and it is preferred that the derivative be pulverized or formed into beads and that the obtained particles be porous. In order to improve the pressure resistance of the separating agent, prevent swelling or contraction caused by solvent substitution and increase the number of theoretical plates, it is preferred that the polysaccharide be supported on a carrier.

When a polysaccharide is used as the powder, it is preferred that the particle size or carrier size be 1 μm to 1 mm, especially 1 to 300 μm, though the preferred size differs to some extent according to the size of the column. It is preferred that the carrier be porous, and have an average pore size of 10 Å to 100 μm, preferably 50 to 5000 Å. The amount of the polysaccharide carbamate derivative supported on the carrier is 1 to 100% by weight, preferably 5 to 50% by weight, based on the carrier.

Either a chemical method or a physical method can be adopted for supporting the polysaccharide carbamate derivative on the carrier. As the physical method, there can be mentioned a method in which the polysaccharide carbamate derivative is dissolved in a solvent capable of dissolving the derivative therein, the solution is sufficiently mixed with the carrier and the solvent is distilled under a reduced pressure or heating or in an air flow, and a method in which the polysaccharide carbamate derivative is dissolved in a solvent capable of dissolving the derivative therein, the solution is sufficiently mixed with the carrier and the mixture is dispersed in a solvent incapable of dissolving the derivative therein to diffuse the former solvent. The obtained separating agent is subjected to an appropriate post-treatment such as heating, addition of a solvent or washing to increase the separating capacity.

A porous organic carrier or a porous inorganic carrier can be used as the carrier, and a porous inorganic carrier is preferred. As suitable examples of the porous organic carrier there can be mentioned polystyrene, polyacrylamide and polyacrylate, and as suitable examples of the porous inorganic carrier, there can be mentioned silica, alumina, magnesia, glass, kaolin, titanium oxide and silicate. The surface of the carrier may be treated to improve the affinity with the polysaccharide carbamate derivative or the surface characteristics of the carrier. As the surface treatment method, there can be mentioned a silane treatment using an organic silane compound and a plasma polymerization surface treatment.

The kind of developing solvent for liquid chromatography or thin-layer chromatography is not particularly critical, so far as it neither dissolves the polysaccharide carbamate derivative nor reacts therewith. When the polysaccharide derivative is chemically bonded with the carrier or is insolubilized by crosslinking, any developing solvent can be used, so far as it does not react with the polysaccharide carbamate derivative.

In case of thin-layer chromatography, a layer of the separating agent composed of particles having a size of 0.1 μm to 0.1 mm and, if necessary, a small amount of a binder, which has a thickness of 0.1 to 100 mm, is formed on a supporting plate.

In the membrane separation method, the separating agent is formed into a hollow yarn or film and is used in this form.

The polysaccharide carbamate derivative of the present invention is very valuable as a functional material and is especially effective for the separation of various compounds, and the polysaccharide carbamate derivative is particularly effective for the separation of optical isomers, which is difficult according to conventional techniques, that is, as a packing for the optical resolution.

The definitions of the terms used in the examples are as follows:

$$\text{Volume ratio } (k') = \frac{[(\text{retention time of enantiomer}) - (\text{dead time})]}{(\text{dead time})}$$

$$\text{Separation coefficient } (\alpha) = \frac{\text{volume ratio of more strongly adsorbed enantiomer}}{\text{volume ratio of more weakly adsorbed enantiomer}}$$

$$\text{Separation degree } (Rs) = \frac{2 \times (\text{distance between peaks of more strongly adsorbed and more weakly adsorbed enantiomers})}{\text{sum of band widths of both peaks}}$$

EXAMPLE 1

Synthesis of Amylose Tris(3,5-Dimethylphenylcarbamate)

1.0 g of amylose (having a molecular weight of about 16,000) was dried in vacuo and 50 ml of dry pyridine was added thereto. The mixture was stirred. 4.0 ml of 3,5-dimethylphenyl isocyanate was added thereto and the obtained mixture was heated with stirring at 100° C. in a nitrogen gas stream for 22 hours. The product mixture was put into methanol to effect precipitation. The obtained precipitates were collected with a glass filter to obtain 2.465 g of amylose tris(3,5-dimethylphenylcarbamate. A yield of the intended product was 66.4 wt.%. The IR analysis of the product was:

|  | C (%) | H (%) | N (%) |
|---|---|---|---|
| obtained | 65.20 | 6.17 | 6.93 |
| calculated | 65.66 | 6.18 | 6.70 |

The product as obtained above was carried on a silica-gel, Lichrospher SI4000, a tradename of the product available from E. Merck, having 10 micron size, and the supported amylose carbamate derivative was packed in a stainless steel column having a length of 25 cm and an inner diameter of 0.46 cm. Optical resolution of various racemic compounds shown in Table 1 was carried out. Good results were obtained as shown in Table 1.

A 9/1 mixed solvent of hexane/2-propanol was used as the solvent. In this table, $k'_1$ represents the retention capacity ratio of the enantiomer first eluted and the parenthesized symbol indicates the optical rotation, while α represents the separation coefficient and Rs indicates the separation degree.

EXAMPLE 2

Starch 3,5-dimethylphenylcarbamate derivative was obtained in the same manner as described in Example 1 except that starch was used instead of amylose.

The optical resolution was conducted with the above obtained carbamate for a racemic mixture in the same way as shown in Example 1, with almost the same results as obtained in Example 1.

TABLE 1

| Racemic Compound *1 | k'1 | α | Rs |
|---|---|---|---|
| benzoin | 3.14 (+) | 1.21 | 2.07 |
| trans-stilbene oxide | 0.42 (+) | 3.40 | 7.88 |
| 2,2'-dihydroxy 6,6'-dimethylbiphenyl | 2.46 (−) | 2.11 | 6.38 |
| 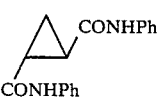 | 3.25 (+) | 2.01 | 3.59 |
| Ph₃C—CH—OH <br> \| <br> Ph | 2.65 (+) | 1.98 | 5.48 |
| 2,2,2-trifluoro-1-(9-anthryl) ethanol | 1.30 (+) | 1.15 | 0.75 |

TABLE 1-continued

| Racemic Compound *1 | k'1 | α | Rs |
|---|---|---|---|
| Troger's base | 0.53 (+) | 1.58 | 2.30 |

Note:
*1: Ph indicates a phenyl group.

EXAMPLE 3

Synthesis of Chitosan-Tris(3,5-Dimethylphenylcarbamate)

Figure 2:
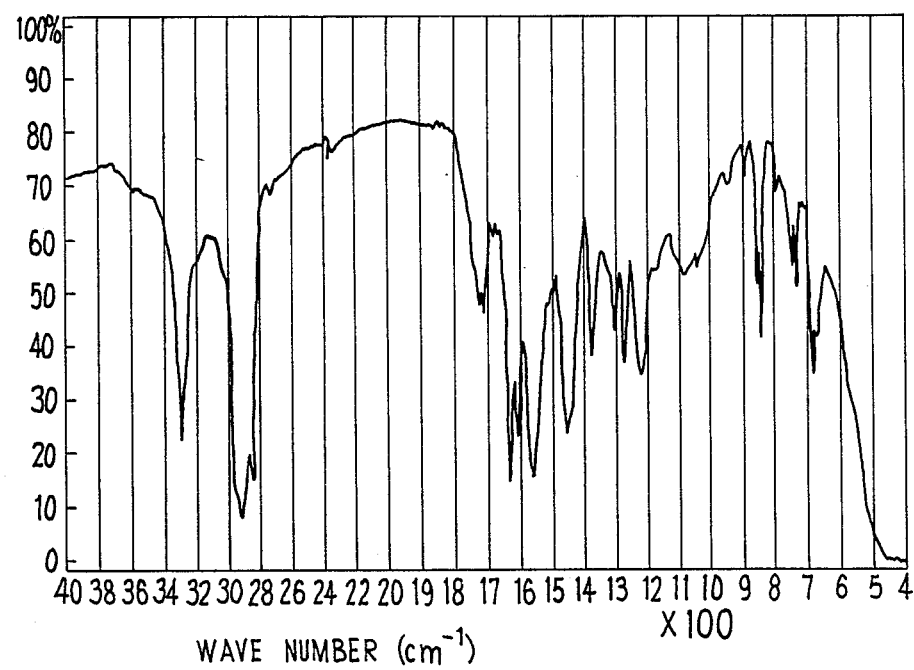

0.801 g of chitosan, 50 ml of pyridine and 5.5 ml of 3,5-dimethylphenyl isocyanate were mixed with one another and heated, while stirred, for reflux, in nitrogen gas. The reaction was continued for 43.5 hours. The product mixture was poured into methanol and the produced precipitates were collected with filteration, followed by washing with methanol. The precipitates were dried at 40° C. for 5 hours at a reduced pressure to obtain 3.418 g of the product. It was examined with IR analysis and the resulting spectrum is shown in FIG. 1. Then the product was dissolved in a solvent mixture of CH3Cl and CF3CH2OH at a volume ratio of 9:1. The soluble portion was analyzed in view of the elementary analysis, a result of which is shown below, and IR analysis, a result of which is shown in FIG. 2.

| | C (%) | H (%) | N (%) |
|---|---|---|---|
| obtained | 68.70 | 6.68 | 9.44 |
| calculated | 68.77 | 6.35 | 9.30 |

Preparation of a Separating Agent

Since it was found that the above obtained product was insoluble in a conventional solvent such as chloroform, tetrahydrofurane and dimethylacetoamide, 0.625 g of the portion of the product which was soluble in the above shown solvent mixture was dissolved in 12 ml of pyridine at about 100° C. After that, 2.60 g of silica-gel, treated with 3-amino-triethoxysilane, available in the tradename of SI-1000, was treated with the obtained solution so that the product might be carried on the silica-gel.

Separation

A column having a length of 25 cm and an inner diameter of 0.46 cm was charged with the obtained separating agent. The separation was conducted for each racemic mixture listed in Table 2 in the same way as shown in Example 1, except that a flow rate was 0.5 ml per minute and the temperature was 25° C. Results are shown in Table 2.

In Table 2, Ph is phenyl, Tr is trityl having the formula of (Ph)3C- and acac is acetylacetonate.

TABLE 2

| test compound | k'1 | α | Rs |
|---|---|---|---|
|  | 0.22 (+) | ~1 | |
| 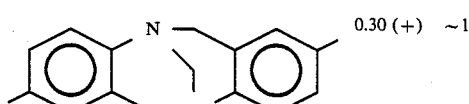 | 0.30 (+) | ~1 | |

TABLE 2-continued

| test compound | k'1 | α | Rs |
|---|---|---|---|
| Ph-CH(OH)-C(=O)-Ph | 1.73 (−) | 1.07 | |
| Tr—CH(OH)—Ph | 0.56 (+) | 1.27 | |
| cyclopropane-1,2-di-CONHPh | 0.90 (−) | 1.33 | 1.10 |
| 2,2'-dimethyl-6,6'-dihydroxybiphenyl | 1.31 (−) | 1.17 | 0.74 |
| 2-Ph-cyclohexanone | 0.53 (−) | 1.10 | |
| 2-Ph-chroman-4-one | 0.65 (−) | 1.11 | 0.75 |
| Co(acac)3 | 4.90 (+) | ~1 | |
| 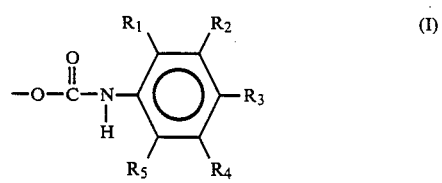 | 1.49 (−) | 1.15 | 0.81 |

What is claimed is:

1. An alkyl-substituted phenylcarbamate derivative of a polysaccharide, exclusive of cellulose and dextran, in which 80 to 100 percent of the hydroxyl groups attached to the polysaccharide have been substituted by an alkyl-substituted phenylcarbamoyl group having the formula (I):

$$-O-\overset{O}{\underset{}{C}}-\underset{H}{N}-\text{C}_6(R_1)(R_2)(R_3)(R_4)(R_5) \quad (I)$$

in which R1 to R5 each are hydrogen or an alkyl having 1 to 8 carbon atoms, provided that at least one of R1 to R5 is the alkyl.

2. A derivative as claimed in claim 1, in which said polysaccharide is optically active.

3. A derivative as claimed in claim 1, in which said polysaccharide has a polymerization degree of 5 to 500.

4. A derivative as claimed in claim 1, in which said group is 3,5-dimethylphenylcarbamoyl.

5. A separating agent comprising the alkyl-substituted phenylcarbamate derivative as defined in claim 1.

6. A separating agent as claimed in claim 5, which is in the form of powder.

7. A separating agent which comprises the derivative as defined in claim 1 and a carrier therefor.

8. A method for separating racemic compounds to an isomer thereof by bringing them in contact with the derivative as defined in claim 1.

9. A method as claimed in claim 8, which is conducted by chromatography.

* * * * *